(12) United States Patent
Chen

(10) Patent No.: US 8,486,922 B2
(45) Date of Patent: Jul. 16, 2013

(54) COMPOSITION

(76) Inventor: Chien-Hung Chen, Taipei (TW)

( * ) Notice: Subject to any disclaimer, the term of this patent is extended or adjusted under 35 U.S.C. 154(b) by 0 days.

(21) Appl. No.: 13/094,938

(22) Filed: Apr. 27, 2011

(65) Prior Publication Data

US 2011/0281829 A1 Nov. 17, 2011

Related U.S. Application Data

(60) Provisional application No. 61/328,819, filed on Apr. 28, 2010.

(51) Int. Cl.
*A61K 31/60* (2006.01)
(52) U.S. Cl.
USPC .............................. 514/165; 514/171; 514/159
(58) Field of Classification Search
USPC .......................... 514/165, 171, 159
See application file for complete search history.

(56) References Cited

FOREIGN PATENT DOCUMENTS

WO   WO2008089212   *   7/2008

OTHER PUBLICATIONS

Konoshenko et al. Antibiotiki, Mar. 1983, 28(3):192-194 (abstract only).*

* cited by examiner

*Primary Examiner* — Rei-tsang Shiao
(74) *Attorney, Agent, or Firm* — Ditthavong Mori & Steiner P.C.

(57) ABSTRACT

This disclosure relates to a pharmaceutical composition that includes a first agent selected from the group consisting of an oxidative phosphorylation inhibitor, an ionophore, and an adenosine 5'-monophosphate-activated protein kinase (AMPK) activator; a second agent that possesses anti-inflammatory activity; and a third agent that is a serotonin metabolite.

14 Claims, No Drawings

COMPOSITION

CROSS-REFERENCES

This application claims priority from U.S. Provisional Patent Application Ser. No. 61/328,819 by Chien-Hung Chen, filed Apr. 28, 2010 and entitled "Novel Composition," the contents of which are incorporated herein in their entirety by this reference.

FIELD OF THE INVENTION

This invention is directed to novel compositions for the treatment of a number of conditions, including hyperproliferative diseases and AIDS.

BACKGROUND OF THE INVENTION

According to the World Health Organization, about five million people die from cancer every year. Drug treatment is one of the three major therapies for cancer. At present, drugs are used to treat cancers by the following mechanisms: interfering with or inhibiting cell division, regulating cell generation cycle, promoting tumor cell apoptosis, inhibiting angiogenesis, inhibiting oncogene activity, promoting tumor-suppressing gene activity, acting as tumor antigens, inhibiting telomerase activities, and interfering with information transfer of tumor cells.

In view of the high mortality rates associated with abnormal proliferative diseases including cancer, there exists a need for an effective treatment for these diseases.

Acquired immunodeficiency syndrome (AIDS), a consequence of infection with the HIV-1 retrovirus, affects over 30 million people worldwide. AIDS is characterized by a number of otherwise very rare opportunistic infections such as Kaposi's sarcoma, caused by the Kaposi's sarcoma-associated herpes virus, *Pneumocystis jirovecii* pneumonia, and other malignancies and infectious diseases. Patients with AIDS also suffer from severe weight loss, night sweats, swollen lymph nodes, and other consequences of a compromised immune system. In AIDS, $CD4^+$ T cells are attacked by the virus and greatly reduced in number. Although treatments for AIDS do exist, including treatment with a "cocktail" of three drugs belonging to at least two classes of antiretroviral drugs, such as, for example, two nucleoside analogue reverse transcriptase inhibitors plus either a protease inhibitor or a non-nucleoside reverse transcriptase inhibitor. Although this approach has proved reasonably successful in inhibiting the growth of HIV-1 and preventing the occurrence of opportunistic infections and other symptoms of AIDS, it is not a cure and the effectiveness of drug therapy can be limited by drug resistance, drug toxicity, and possible patient non-compliance. Therefore, there is a need for an improved therapy for AIDS.

SUMMARY OF THE INVENTION

This disclosure is based on the unexpected discovery that a combination of certain known drugs or compounds is effective in treating hyperproliferative diseases (including cancer), as well as other diseases, including AIDS.

In one aspect, the present disclosure features a pharmaceutical composition that includes: (1) a first agent that can be an oxidative phosphorylation inhibitor, an ionophore, or an adenosine 5'-monophosphate-activated protein kinase (AMPK) activator, (2) a second agent that possesses anti-inflammatory activity, and (3) a third agent that is a serotonin metabolite (e.g., 5-hydroxyindoleacetic acid). The term "oxidative phosphorylation inhibitor" refers to a suitable agent that inhibits oxidative phosphorylation, such as oxidative phosphorylation uncouplers. An ionophore is a lipid-soluble molecule capable of transporting an ion across the lipid bilayer of cell membranes. An AMPK activator is an agent that activates AMPK to phosphorylate its substrates, e.g., acetyl-CoA carboxylase and malonyl-CoA decarboxylase. Examples of the first agent include metformin (e.g., metformin hydrochloride), phenformin, buformin, ephedrine, thyroxine, salicylanilide, and salicylic acid. The second agent can be a suitable anti-inflammatory compound (e.g., non-steroidal anti-inflammatory compound). Examples include aspirin, diclofenac (e.g., diclofenac potassium or diclofenac sodium), ibuprofen (e.g., dexibuprofen or dexibuprofen lysine), indomethacin, acetaminophen, nimesulide, and a COX-2 inhibitor (e.g., a nitric oxide-based COX-2 inhibitor). A preferred composition contains metformin hydrochloride, aspirin, and 5-hydroxyindoleacetic acid, or metformin hydrochloride, aspirin, and 5-hydroxyindoleacetic acid creatinine sulfate complex. The three agents mentioned above can treat a target disease via biological mechanisms other than those described therein. For example, metformin may treat a target disease (e.g., cancer) via a mechanism other than inhibiting oxidative phosphorylation or activating AMPK. In one alternative, one or more of the first agent, the second agent, and the third agent can be individually bound to their own individual carrier substances that facilitate the transport of the first agent, the second agent, or the third agent to their intended site of action; the individual carrier substances can be, but are not limited to, antibodies, hormones, receptor agonists or antagonists, or receptors. The first agent, the second agent, or the third agent can be covalently or noncovalently bound to their individual carrier substances.

The composition described above can contain 5-5,000 mg (e.g., 5-3,000 mg, 5-1,500 mg, or 5-1,000 mg) of the first agent, 1-5,000 mg (e.g., 1-3,000 mg, 1-1,000 mg, 1-500 mg, or 1-100 mg) of the second agent, and 0.1-1,000 mg (e.g., 0.1-100 mg, 0.1-50 mg, or 0.1-30 mg) of the third agent, or in quantities of the same ratio as calculated based on the above amounts.

In another aspect, this disclosure features a method for treating a disease by administering the above-described pharmaceutical composition to a subject in need of the treatment. The disease includes metabolic syndrome, obesity, hypertension, diabetes, Parkinson's disease, polycystic ovarian syndrome, a hyperproliferative disease (e.g., benign or malignant tumors), AIDS, Alzheimer's disease, osteoporosis, sleep apnea, erectile dysfunction, McArdle disease, and a metabolism disorder.

In yet another aspect, the present disclosure features a method for reducing aging or fatigue by administering the above-described pharmaceutical composition to a subject in need of the treatment.

Also within the scope of this disclosure is the use of the above-described composition for the manufacture of a medicament for any of the diseases and disorders mentioned above.

The details of one or more embodiments of the disclosure are set forth in the description below. Other features, objects, and advantages of the disclosure will be apparent from the description and from the claims.

DETAILED DESCRIPTION

Disclosed herein is use of a composition for treating various diseases/disorders. The composition includes at least three active agents which are described immediately below and also in U.S. Application Publication Nos. 2008/0176822 and 2009/0286760,as well as U.S. application Ser. No. 12/723,771, all of which are incorporated herein in their entirety by this reference.

The first agent can include, in addition to those described above, 4,6-dinitro-o-cresol, uncoupling proteins (e.g., UCP1, UCP2, or UCP3), carbonyl cyanide p-(trifluoromethoxy)phenyl-hydrazone, carbonyl cyanide m-chlorophenyl-hydrazone, C5 gene products, dinitrophenol (e.g., 2,4-dinitrophenol), efrapeptin (A23871), guanethidine, chlorpromazine, amytal, secobarbital, rotenone, progesterone, antimycin A, naphthoquinone, 8-hydroxyquinoline, azides (e.g., $NaN_3$), dicoumarin, bilirubin, bile pigment, ephedrine, hydrogen sulfide, tetraiodothyronine, quercetin, 2,4-bis(p-chloroanilino) pyrimidine, glyceraldehyde-3-phosphate dehydrogenase, oligomycin, tributyltin chloride, aurovertin, rutamycin, venturicidin, dicyclohexylcarbodiimide, Dio-9, m-chlorophenyl-hydrazone mesoxalonitrile, ionomycin, calcium ionophores (e.g., A23187 (calcimycin), NMDA, CA 1001 ((–)-(R,R)-N,N'-bis[11-(ethoxycarbonyl)undecyl]-N,N'-4,5-tetramethyl-3,6-dioxaoctanediamide), or enniatin B), compounds that increase the $Ca^{+2}$ concentration in mitochondria (e.g., atractyloside, bongkrekic acid, thapsigargin, amino acid neurotransmitters, glutamate, N-methyl-D-aspartic acid, carbachol, ionophores, inducers of potassium depolarization), valinomycin, gramicidin, nonactin, nigericin, lasalocid, and monensin. These compounds fall into the general categories of: (1) oxidative phosphorylation inhibitors or (2) ionophores.

In another alternative, the first agent can be an AMPK activator. AMPK activators include, but are not limited to:
(1) metformin;
(2) phenformin;
(3) buformin;
(4) AICAR;
(5) thienopyridones;
(6) resveratrol;
(7) nootkatone;
(8) thiazole;
(9) adiponectin;
(10) 2-deoxyglucose;
(11) AAPDs (atypical antipsychotic drugs, including olanzapine, quetiapine, and risperidone);
(12) adiponectin variant polypeptides such as AdipoR3v1 polypeptide, AdipoRe polypeptide, and AdipoR2vs polypeptide, disclosed in U.S. Pat. No. 7,435,808 to Wu et al., incorporated herein by this reference;
(13) catechins, including catechin, gallocatechin, catechin gallate, gallocatechin gallate, epicatechin, epigallocatechin, epicatechin gallate and epigallocatechin gallate, disclosed in United States Patent Application Publication No. 2007/0004650 by Shimotoyodome et al., incorporated herein by this reference;
(14) trans-10, cis-12 conjugated linoleic acid;
(15) corydaline and related compounds, including corlumidin, (+)-corlumidin, corypalmine, 14R-(+)-corypalmine, tetrahydropalmatine, 14R-(+)-tetrahydropalmatine, 14R, 13S-(+)-corydaline, bicuculline, d-(+)-bicuculline, egenine, and +-egenine, disclosed in United States Patent Application Publication No. 2009/0042810 by Chung and United States Patent Application Publication No. 2009/048246 by Lin et al., both of which are incorporated herein by this reference;
(16) dithiolethiones, including oltipraz and 5-(4-methoxyphenyl)-3H-1,2-dithiole-3-thione;
(17) inhibitors or antagonists of DNA-dependent protein kinase catalytic subunit (DNA-PKcs), disclosed in United States Patent Application Publication No. 2010/0130597 by Chung et al., incorporated herein by this reference;
(18) small interfering RNAs (siRNAs) that can inhibit the expression and/or translation of DNA-PKcs, disclosed in United States Patent Application Publication No. 2010/0130597 by Chung et al., incorporated herein by this reference;
(19) fibrates, including bezafibrate, ciprofibrate, fenofibrate, clofibrate, and gemfibrozil;
(20) GW2974 (N4-(1-benzyl-1H-indazol-5-yl)-N6,N6-dimethyl-pyrido-[3,4-d]-pyrimidine-4,6-diamine);
(21) honokiol;
(22) leptin;
(23) LKB1 (serine/threonine kinase 11);
(24) obovatol (4',5-diallyl-2,3-dihydroxybiphenyl ether);
(25) pioglitazone and related thiazolidinediones, including rosiglitazone and rosiglitazone maleate;
(26) Y122S/I125E and additional muteins of adiponectins, disclosed in U.S. Pat. No. 7,678,886 to Zalevsky et al., incorporated herein by this reference, such as a variant adiponectin peptide with the formula: V(109)-V(110)-V(111)-F(112)-F(113-121)-V(122)-F(123)-V(124)-V(125)-F(126-127)-V(128)-F(129-134)-V(135)-F(136-151)-V(152)-F(153-163)-F-(164)-F(165-181)-V(182)-F(183)-V(184)-F(185-206)-V(207)-F(208-220)-F(221)-F(222-223)-V(224)-V(225)-F(226)-V(227)-F(228)-V(229), wherein V(109) is selected from the group consisting of: the wild-type amino acid V; any of variant amino acids D, E, H, K, N, Q, and R; and, a deletion of V109; V(110) is selected from the group consisting of: the wild-type amino acid V; any of variant amino acids D, E, H, K, N, Q, R, and S; and, a deletion of V110; V(111) is selected from the group consisting of: the wild-type amino acids Y and H; any of variant amino acids D, E, N, R, and S; and, a deletion of 111; F(112) is selected from the group consisting of the wild-type amino acids R and C, and, a deletion of 112; F(113-121) is selected from the group consisting of: the wild-type amino acid sequence SAFSVGLET; and, a deletion of any of S113, A114, F115, S116, V117, G118, L119, E120, and T121; V(122) is selected from the group consisting of: the wild-type amino acid Y; any of variant amino acids D, E, H, N, R, and S; and, a deletion of Y122; F(123) is selected from the group consisting of: the wild-type amino acid sequence V and a deletion of V123; V(124) is selected from the group consisting of: the wild-type amino acid T; any of variant amino acids D, E, K, N, and R; and, a deletion of T124; V(125) is selected from the group consisting of: the wild-type amino acid I; any of variant amino acids D, E, H, K N, Q, R, S, and T; and, a deletion of I125; F(126-127) comprises the wild-type amino acid sequence PN; V(128) is selected from the group consisting of: the wild-type amino acid M; and any of variant amino acids A, D, E, H, K, N, Q, R, S, and T; F(129-134) comprises the wild-type amino acid sequence PIRFTK; V(135) is selected from the group consisting of: the wild-type amino acid I; and, any of variant amino acids D, E, H, K, N, Q and R; F(136-151) comprises the wild-type amino acid sequence FYNQQNHYDGSTGKFH; V(152) is selected from the group consisting of: the wild-type amino acid C; and, any of variant amino acids A, F, L, N, S, T and V; F(153-163) comprises the wild-type amino acid sequence NIPGLYYFAYH; F(164) is selected from the group consisting of the wild-type amino acid I and T; F(165-181) comprises the wild-type amino acid sequence TVYMKDVKVSLFKKDKA; V(182) is selected from the group consisting of: the wild-type amino acid M; and, any of variant amino acids A, D, E, K, N, Q, R, S, and T; F(183) comprises the wild-type amino acid L; V(184) is selected from the group consisting of: the wild-type amino acid F; and, any of variant amino acids D, H, K, N and R; F(185-206) comprises the wild-type amino acid sequence TYDQYQENNVDQASGSVLLHLE; V(207) is selected from the group consisting of: the wild-type amino acid V; and, any of variant amino acids D, E, H, K, N, Q, R, and S; F(208-220) comprises the wild-type amino acid sequence GDQVWLQVYGEGE; F(221) is selected from the group consisting of the wild-type amino acids R and S; F(222-223) comprises the wild-type amino acid sequence NG; V(224) is selected from the group consisting of: the wild-type amino acid L; and, any of variant amino acids D, E, H, K, N, Q, R and S; V(225) is selected from the group consisting of: the wild-type amino acid Y; and, any of variant amino acids D, E, H, K, N, Q, R and S; F(226) comprises the wild-type amino acid A; V(227) is selected from the group consisting of: the wild-type amino acid D; and, any of variant amino acids H, K and R; F(228) comprises the wild-type amino acid N; or V(229) is selected from the group consisting of: the wild-type amino acid D; and, any of variant amino acids H, K and R, the variant adiponectin having at least threefold increased solubility when compared to wild-type adiponectin; and the salts, solvates, analogues, congeners, bioisosteres, hydrolysis products, metabolites, precursors, and prodrugs thereof. It is generally preferred that the first agent is an AMPK activator.

In another alternative, the first agent can be selected from the group consisting of ephedrine, thyroxine, salicylanilide, or salicylic acid; and the salts, solvates, analogues, congeners, bioisosteres, hydrolysis products, metabolites, precursors, and prodrugs thereof.

The second agent can include steroidal anti-inflammatory drugs and non-steroidal anti-inflammatory drugs.

Typically, steroidal anti-inflammatory drugs suitable for use in compositions and methods of the present invention are glucocorticoids, or steroids that have glucocorticoid activity. Such steroids may also have a certain degree of mineralocorticoid activity, but anti-inflammatory activity of steroidal anti-inflammatory drugs is closely associated with their glucocorticoid activity.

Ether derivatives of the steroid dexamethasone are disclosed in U.S. Pat. No. 5,223,493. These derivatives include, but are not limited to, 9α-fluoro-11β,17α-dihydroxy-21-methoxy-16α-methylpregna-1,4-diene-3,20-dione, 9α-fluoro-11β,17α-dihydroxy-21-benzyloxy-16α-methyl-pregna-1,4-diene-3,20-dione, 9α-fluoro-11β,17α-dihydroxy-21-(2-methoxyethoxy)methoxy-16α-methylpregna-1,4-diene-3,20-dione, 9α-fluoro-11β,17α-dihydroxy-21-(2-hydroxylethoxy)-16α-methylpregna-1,4-diene-3,20-dione, 9α-fluoro-11β,17α-dihydroxy-21-(methylthiomethoxy)-16α-methylpregna-1,4-diene-3,20-dione, 9α-fluoro-11β,17α-dihydroxy-21-(methoxy)methoxy-16α-methylpregna-1,4-diene-3,20-dione, 9α-fluoro-11β,17α-dihydroxy-$\Delta_{20}$-ethoxy-21-ethoxy-16α-methylpregna-1,4-diene-3,20-dione, 9α-fluoro-11β,17α-dihydroxy-21-ethoxy-16α-methylpregna-1,4-diene-3,20-dione, 9α-fluoro-11β,17α-dihydroxy-21-allyloxy-16α-methylpregna-1,4-diene-3,20-dione, 9α-fluoro-11β,17α-dihydroxy-21-cyclopropylmethoxy-16α-methylpregna-1,4-diene-3,20-dione, 9α-fluoro-11β,17α-dihydroxy-21-allyl-21-allyloxy-16α-methyl-1,4-diene-3,20-dione, 9α-fluoro-11β,17α-hydroxy-21-isopropyloxy-16α-methylpregna-1,4-diene-3,20-dione, 9α-fluoro-11β-propionoxy-17α-hydroxy-21-methoxy-16α-methylpregna-3,20-dione, and 9α-fluoro-11β-17α-diacetoxy-21-methoxy-16α-methylpregna-1,4-diene-3,20-dione.

Reactions of steroids are well known in the art, and need not be described further here. Many steroids undergo esterification at one or more hydroxyl residues with an acyl radical to form ester derivatives. Ether derivatives of steroids can be formed by the Williamson ether synthesis or other ether-forming reactions known in the art. Steroids are also subject to halogenation and other modification reactions.

Examples of steroidal anti-inflammatory drugs include:

(1) hydrocortisone (including esters such as hydrocortisone acetate, hydrocortisone butyrate, hydrocortisone cypionate, hydrocortisone sodium phosphate, hydrocortisone sodium succinate, and hydrocortisone valerate);

(2) cortisone;

(3) beclomethasone (including esters such as beclomethasone propionate, beclomethasone dipropionate;

(4) betamethasone (including esters such as betamethasone dipropionate, betamethasone sodium phosphate, and betamethasone valerate);

(5) dexamethasone (including esters such as dexamethasone acetate and dexamethasone sodium phosphate);

(6) prednisone;

(7) methylprednisolone (including esters such as methylprednisolone acetate and methylprednisolone sodium succinate);

(8) triamcinolone (including acetonide derivatives such as triamcinolone acetonide and triamcinolone hexacetonide and other derivatives such as triamcinolone benetonide as well as esters such as triamcinolone diacetate);

(9) fluocinolone (including acetonide derivatives such as fluocinolone acetonide);

(10) fludrocortisone (including esters such as fludrocortisone acetate);

(11) hyaluronic acid 6-methylprednisolone ester;

(12) rimexolone;

(13) deflazacort,

(14) prednisolone (including esters such as prednisolone farnesylate, prednisolone acetate, prednisolone sodium phosphate, prednisolone 25-diamino-acetate, and prednisolone tebutate);

(15) ORG6632 (21-chloro-9α-11β-hydroxy-16α,17α-dimethylpregna-1,4-diene-3,20-dione);

(16) 21-acetoxypregnenolone;

(17) alclometasone;

(18) algestone;

(19) amcinonide;

(20) azulfidine;

(21) budesonide;

(22) chloroprednisone;

(23) clobetasol (including esters such as clobetasol propionate);

(24) clocortolone (including esters such as clocortolone pivalate);

(25) cloprednol;

(26) corticosterone;

(27) desonide;

(28) desoximetasone;

(29) desoxycorticosterone (including esters such as desoxycorticosterone acetate);

(30) diflorasone;

(31) difluprednate;

(32) enoxolone;

(33) fluazacort;

(34) flucloronide;

(35) flumethasone;

(36) flunisolide;

(37) fluocortolone;

(38) fluorometholone;

(39) fluprednidene (including esters such as fluprednidene acetate);

(40) fluprednisolone;

(41) fluticasone (including esters such as fluticasone propionate);

(42) halcinonide;
(43) halobetasol (including esters such as halobetasol propionate);
(44) halometasone;
(45) hydrocortamate;
(46) medrysone;
(47) meprednisone;
(48) mometasone (including esters such as mometasone furoate);
(49) paramethasone;
(50) prednicarbate;
(51) prednival;
(52) prednylidene;
(53) tixocortol;
(54) clobetasone;
(55) cortivazol;
(56) diflucortolone;
(57) fluocinolone (including acetonide derivatives such as fluocinolone acetonide);
(58) fluocortin (including esters such as fluocortin butyl);
(59) fluperolone (including esters such as fluperolone acetate);
(60) formocortal;
(61) halopredone (including esters such as halopredone acetate);
(62) mazipredone;
(63) 6α,9α-difluoro-17α-[(2-furanylcarbonyl)oxy]-11β-hydroxy-16α-methyl-3-oxoandrosta-1,4-diene-17β-carbothioic acid S-fluoromethyl ester;
(64) 6α,9α-difluoro-11β-hydroxy-16α-methyl-3-oxo-17α-propionyloxy-androsta-1,4-diene-17β-carbothioic acid S-(2-oxo-tetra hydrofuran-3S-yl) ester;
(65) rofleponide;
(66) ciclesonide;
(67) butixocort (including esters such as butixocort propionate);
(68) RPR-106541 (20R-16α,17α-[butylidenebis(oxy)]-6α,9α-difluoro-11β-hydroxy-17β-(methylthio)androsta-4-en-3-one);
(69) ST-126 (9-Fluoro-11β,17,21-trihydroxy-16α-methyl-1,4-pregnadiene-3,20-dione 21-cyclohexanecarboxylate cyclopropanecarboxylate);
(70) flurandrenolide;
(71) 9α-fluoro-11β,17α-dihydroxy-21-methoxy-16α-methylpregna-1,4-diene-3,20-dione;
(72) 9α-fluoro-11β,17α-dihydroxy-21-benzyloxy-16α-methylpregna-1,4-diene-3,20-dione;
(73) 9α-fluoro-11β,17α-dihydroxy-21-(2-methoxyethoxy)methoxy-16α-methylpregna-1,4-diene-3,20-dione;
(74) 9α-fluoro-11β,17α-dihydroxy-21-(2-hydroxylethoxy)-16α-methylpregna-1,4-diene-3,20-dione;
(75) 9α-fluoro-11β,17α-dihydroxy-21-(methylthiomethoxy)-16α-methylpregna-1,4-diene-3,20-dione
(76) 9α-fluoro-11β,17α-dihydroxy-21-(methoxy)methoxy-16α-methylpregna-1,4-diene-3,20-dione;
(77) 9α-fluoro-11β,17α-dihydroxy-Δ20-ethoxy-21-ethoxy-16α-methylpregna-1,4-diene-3,20-dione;
(78) 9α-fluoro-11β,17α-dihydroxy-21-ethoxy-16α-methylpregna-1,4-diene-3,20-dione;
(79) 9α-fluoro-11β,17α-dihydroxy-21-allyloxy-16α-methylpregna-1,4-diene-3,20-dione;
(80) 9α-fluoro-11β,17α-dihydroxy-21-cyclopropylmethoxy-16α-methylpregna-1,4-diene-3,20-dione;
(81) 9α-fluoro-11β,17α-dihydroxy-21-allyl-21-allyloxy-16α-methyl-1,4-diene-3,20-dione;
(82) 9α-fluoro-11β,17α-hydroxy-21-isopropyloxy-16α-methylpregna-1,4-diene-3,20-dione;
(83) 9α-fluoro-11β-propionoxy-17α-hydroxy-21-methoxy-16α-methylpregna-3,20-dione; and
(84) 9α-fluoro-11β-17α-diacetoxy-21-methoxy-16α-methylpregna-1,4-diene-3,20-dione;
and the esters, acetonides, benetonides, furetonides, salts, solvates, analogues, congeners, bioisosteres, hydrolysis products, metabolites, precursors, and prodrugs thereof.

Examples of non-steroidal anti-inflammatory drugs (NSAIDs) include:
(1) A183827;
(2) ABT963 ((2-(3,4-difluoro-phenyl)-4-(3-hydroxy-3-methyl-butoxy)-5-(4-methanesulfonyl-phenyl)-2H-pyridazin-3-one);
(3) aceclofenac;
(4) acemetacin;
(5) acetaminophen;
(6) acetylsalicylic acid;
(7) ACP (4-[bis(acetyloxy)methyl]-1,2-benzenediol diacetate);
(8) actarit (4-(acetylamino)phenylacetic acid);
(9) AHR10037 (2-amino-3-(4-chlorobenzoyl)benzeneacetamide);
(10) AHR15010 (1-[(2-methoxyphenoxy)methyl-1,2-ethanediyl ester of sulfamic acid)
(11) alclofenac;
(12) alminoprofen;
(13) amfenac;
(14) ampiroxicam
(15) amtolmetin guacil;
(16) apazone;
(17) araprofen;
(18) atliprofen methyl ester;
(19) AU8001 (4'-acetamidophenyl-2-(5'-4-tolyl-1'-methylpyrrole)acetate);
(20) azapropazone;
(21) bendazac;
(22) benoxaprofen;
(23) benzydamine;
(24) benzydamine flufenamate;
(25) bermoprofen;
(26) benzpiperylon;
(27) BF388 (1-(3,5-di-tert-butyl-4-hydroxyphenyl)pyrrolidin-2-one);
(28) BF389 (dihydro-4-[[3,5-bis(1,1-dimethyl)-4-hydroxyphenyl]methylene]-2-methyl-2H-1,2-oxazin-3(4H)-one);
(29) BIRL790 (6-chloro-4-[(1-methylethyl)sulfonyl]-2-(phenylmethyl)-1,3(2H,4H)-isoquindinedione);
(30) BMS347070 ((Z)-3-(1-(4-bromophenyl)-1-(4-methylsulfonylphenyl)methylidine)-dihydrofuran-2-one, a COX-2 inhibitor);
(31) bromfenac;
(32) bucloxic acid;
(33) bumadizone;
(34) butibufen;
(35) BW4C ((N-(3-phenoxy-phenyl-2-propenyl)acetohydroxamic acid);
(36) BW755C ((3-amino-1-[m-(trifluoromethyl)phenyl]-2-pyrazoline);
(37) C53;
(38) C73;
(39) C85;
(40) carprofen;
(41) CBS1108 (2-acetylthiophene-2-thiazolylhydrazone);
(42) celecoxib;
(43) CGS25997 ((2S)-(–)-2-[[N-(aminocarbonyl)-N-hydroxyamino]methyl-7-fluoroxyphenyl-1,4-benzodioxan);
(44) CHF2003;

(45) chlorobiphenyl;
(46) choline magnesium trisalicylate;
(47) CHX108 (a lipoxygenase/cyclooxygenase inhibitor);
(48) CI959 (5-methoxy-3-(1-methylethoxy)-N-1H-tetrazol-5-yl-benzo9b]thiophene-2-carboxamide sodium salt);
(49) cimicoxib;
(50) cinmetacin;
(51) cinnoxicam;
(52) clidanac;
(53) clofezone;
(54) clonixin;
(55) clopirac;
(56) CLX1205;
(57) COX-2 inhibitors;
(58) CP331 (N-(3-[3-(piperidinyl-methyl)phenoxy]propyl)-carbamoyl-methylthio]ethyl 1-(p-chlorobenzoyl) 5-methoxy-2-methyl-3-indolyl-acetate);
(59) CS502 (a COX-2 inhibitor);
(60) CS706 (2-(4-ethoxyphenyl)-4-methyl-1-(4-sulfamoylphenyl)-1H-pyrrole);
(61) D1367 (a COX-2 inhibitor);
(62) darbufelone;
(63) deracoxib;
(64) dexibuprofen;
(65) dexibuprofen lysine;
(66) dexketoprofen;
(67) DFP;
(68) DFU ((5,5-dimethyl-3-(3-fluorophenyl)-4-(4-methylsulphonyl)phenyl-2(5H)-furanone);
(69) diclofenac sodium;
(70) diclofenac potassium;
(71) diflunisal;
(72) DP155 (mixture of 1-steroyl and 1-palmitoyl-2-{4-[1-(p-chlorobenzoyl)-5-methoxy-2-methyl-3-indolyl acetamido]hexanoyl}-sn-glycero-3-phosphatidyl choline);
(73) DRF4367 (2-hydroxymethyl-4-(5-(4-methoxyphenyl)-3-trifluoromethyl-1H-1-pyrazolyl)-1-benzenesulfonamide);
(74) droxicam;
(75) E5110 (N-methoxy-3-(3,5-di-tert-butyl-4-hydroxybenzylidene pyrrolidin-2-one);
(76) E6080 (4-[[(6-hydroxy-4,4-7-trimethyl-2-benzothiazolyl)amino]methyl]benzenesulfonamide monohydrochloride);
(77) E6087 (4-(5-(2,4-difluorophenyl)-4,5-dihydro-3-trifluoromethyl-1H-pyrazol-1-yl)benzenesulfonamide);
(78) eltenac;
(79) enfenamic acid;
(80) epirizole;
(81) ER34122 (5-[1-[1,5-bis(4-methoxyphenyl)pyrazol-3-yl]-1,1-dimethoxymethyl]-2-chlorobenzamide);
(82) esflurbiprofen;
(83) ethenzamide;
(84) etodolac;
(85) etofenamate;
(86) etoricoxib;
(87) F025;
(88) FCE20696 ((6H-dibenzo[b,d]pyran-6-carboxylic acid 2-(dimethylamino)ethyl ester hydrochloride);
(89) felbinac;
(90) felbinac ethyl;
(91) fenbufen;
(92) fenclofenac;
(93) fenclozic acid;
(94) fenclozine;
(95) fendosal;
(96) fenoprofen;
(97) fentiazac;
(98) fepradinol (α-[[(2-hydroxy-1,1-dimethylethyl)amino]methyl]benzenemethanol);
(99) feprazone;
(100) filenadol;
(101) flobufen;
(102) florifenine;
(103) flosulide;
(104) flubichin methanesulfonate;
(105) flufenamic acid;
(106) flufenisal;
(107) flunixin;
(108) flunoxaprofen;
(109) fluprofen;
(110) fluproquazone;
(111) flurbiprofen;
(112) FPL62064 (N-(4-methoxyphenyl)-1-phenyl-1H-pyrazole-3-amine);
(113) FR111142 (4,5-dihydroxy-2-hexenoic acid 5-methoxy-4-[2-methyl-3-(3-methyl-2-butenyl)oxiranyl]-1-oxaspiro[2.5]oct-6-yl ester);
(114) FR 122047 (1-[[4,5-bis(4-methoxyphenyl)-2-thiazolyl]carbonyl]-4-methylpiperazine hydrochloride; a COX-1 inhibitor);
(115) FR123826 (a COX-2 inhibitor);
(116) FR140423 (3-(difluoromethyl)-1-(4-methoxyphenyl)-5-[4-(methylsulfinyl)phenyl]pyrazole; a COX-2 inhibitor);
(117) FR188582 (3-chloro-5-[4-(methylsulfonyl) phenyl]-1-phenyl-1H-pyrazole; a COX-2 inhibitor);
(118) FS205397 (an analgesic);
(119) furofenac;
(120) GR80907;
(121) GR129574A ((R)-N[1-carboxy-3-(1,3-dihydro-1,3-dioxo-2Hbenz[f]isoindol-2-yl)propyl]-L-leucyl-N-methyl-L-phenylalanamide);
(122) GR253035 (a COX-2 inhibitor);
(123) GW406381 (a COX-2 inhibitor);
(124) HAI105;
(125) HAI106;
(126) HCT2035 (NO-ketoprofen or toprofen);
(127) HGP12;
(128) HN3392;
(129) HP977 (3-(6,11-dihydro-11-oxodibenz(b,e)oxepin-2-yl)-N-hydroxy-N-methylpropanamide);
(130) HX0835;
(131) HYAL AT2101 (a topical gel of hyaluranon and 3% diclofenac);
(132) ibufenac;
(133) ibuprofen;
(134) ibuproxam-beta-cyclodextrin;
(135) icodulinum;
(136) IDEA070 (a COX-1, COX-2, and lipoxygenase inhibitor);
(137) iguratimod;
(138) imrecoxib;
(139) indomethacin;
(140) indoprofen;
(141) IP751 (ajulemic acid);
(142) IRA378 ((S)-8-chloro-1,2,3,4-tetrahydro-2-(trifluoromethyl)-6-quinolineacetic acid);
(143) isofezolac;
(144) isoxepac;
(145) isoxicam;
(146) IX207887 (10-methoxy-4H-benzo[4,5]cyclohepta(1,2-b)thiophene-4-yliden)acetic acid);

(147) KC764 (2-methyl-3-(1,4,5,6-tetrahydronicotinoyl) pyrazolo[1,5-a]pyridine);
(148) ketoprofen;
(149) ketorolac;
(150) L652343 (3-hydroxy-5-trifluoromethyl-N-[2-(2-thienyl)-2-phenyl-ethenyl]-benzo(B) thiophene-2-carboxamide);
(151) L745337 (5-methanesulfonamido-6-(2,4-difluorothiophenyl)-1-indanone);
(152) L748731 (a COX-2 inhibitor);
(153) L752860 (5,5-dimethyl-4-(4-(methylsulfonyl)phenyl)-3-(3-fluorophenyl)-5H-furan-2-one);
(154) L651392 (4-bromo-2,7-dimethoxy-3H-phenothiazin-3-one);
(155) L663536 (3-[3-butylsulfanyl-1-[(4-chlorophenyl) methyl]-5-propan-2-yl-indol-2-yl]-2,2-dimethyl-propanoic acid);
(156) L761066 (a COX-2 inhibitor);
(157) L768277 (a substituted 5,6-diarylthiazolo[3,2-b][1,2,4]triazole; a COX-2 inhibitor);
(158) L776967;
(159) L783003;
(160) L784520;
(161) L791456 (5-chloro-2-methylpyridin-3-yl)-3-(4-methylsulfonylphenyl)pyridine, a COX-2 inhibitor);
(162) L804600 (2-benzyl-4-isopropoxy-5-[4-(methylsulfonyl)phenyl]pyridazin-3(2H)-one);
(163) L818571 (2-(cyclopropylmethyl)-4-(4-fluorophenyl)-5-[4-(methylsulfonyl)phenyl]pyridazin-3(2H)-one);
(164) LAS33815 (4-(2,3-dihydro-2-oxo-3-phenyl-4-oxazolyl)-benzenesulfonamide);
(165) LAS34475 (a COX-2 inhibitor);
(166) licofelone;
(167) LM4108 (([1-(4-chlorobenzoyl)-5-methoxy-2-methyl-1H-indol-3-yl]-N-phenethyl-acetamide or indomethacin phenethylamide);
(168) lobuprofen;
(169) lomoxicam;
(170) lonazolac;
(171) loxaprofen;
(172) lumaricoxib;
(173) LY221608 (5-[[3,5-bis(1,1-dimethylethyl)-4-hydroxyphenyl]methylene]-3-(dimethylamino)-4-thiazolidinone);
(174) LY269415 (5-[[3,5-bis(1,1-dimethylethyl)-4-hydroxyphenyl]methylene]-3-(methylamino)-4-thiazolidinone);
(175) mabuprofen;
(176) meclofenamic acid;
(177) meclofenamate sodium;
(178) mefenamic acid;
(179) meloxicam;
(180) mercaptoethylguanidine;
(181) mesaclazone;
(182) mesoporphyrin;
(183) metoxibutropate;
(184) miroprofen;
(185) mofebutazone;
(186) mofezolac;
(187) morazone;
(188) MX1094 (a prodrug of naproxen);
(189) nabumetone;
(190) naproxen sodium;
(191) naproxen sodium/metoclopramide;
(192) NCX1101 (nitric oxide donor grafted to a conventional drug);
(193) NCX284 (NO-diclofenac);
(194) NCX285 (NO-diclofenac);
(195) NCX4016;
(196) NCX4215;
(197) NCX530 (a nitric-oxide-releasing derivative of indomethacin, 1-(4-chlorobenzoyl)-5-methoxy-2-1H-indole-3-acetic acid 3-(nitrooxymethyl)phenyl ester));
(198) nepafanac;
(199) niflumic acid;
(200) nimesulide;
(201) nitric oxide-based NSAIDs (NitroMed, Lexington, Mass.);
(202) nitrofenac;
(203) nitroflurbiprofen;
(204) nitronaproxen;
(205) NS398 (N-[2-cyclohexyloxy-4-nitrophenyl]methanesulfonamide);
(206) ocimum sanctum oil;
(207) olsalazine;
(208) ONO3144 (2-amino-4-t-butyl-6-propionylphenol);
(209) orpanoxin;
(210) oxaceprol;
(211) oxaprozin;
(212) oxindanac;
(213) oxpinac;
(214) oxycodone/ibuprofen;
(215) oxyphenbutazone;
(216) P10294 (3-(6,11-dihydrodibenz[b,e]oxepin-2-yl)-N-hydroxy-N-methylpropanamide);
(217) P54 (a phytochemical-based selective COX-2 inhibitor);
(218) P8892 (a cyclooxygenase/lipoxygenase inhibitor);
(219) pamicogrel;
(220) parcetasal;
(221) parecoxib;
(222) parsalmide;
(223) PD138387 ((Z)-5-(3,5-di-tert-butyl-4-hydroxybenzylidene)-2-(methoxyamino)thiazol-4(5H)-one, a COX-2 inhibitor);
(224) PD145246;
(225) PD164387 (2,6-di-tert-butyl-4-[5-(ethylsulfanyl)-1,3,4-thiadiazol-2-yl]phenol);
(226) pelubiprofen;
(227) pemedolac;
(228) phenylbutazone;
(229) pirazolac;
(230) piroxicam;
(231) piroxicam beta-cyclodextrin;
(232) piroxicam pivalate;
(233) pirprofen;
(234) pranoprofen;
(235) prinomide (α-cyano-1-methyl-b-oxopyrrole-2-propionanilide with 2-amino-2-(hydroxymethyl)-1,3-propanediol);
(236) proglumetacin;
(237) resveratrol;
(238) R-ketoprofen;
(239) R-ketorolac;
(240) Ro323555 (β-(cyclopentylmethyl)-N-hydroxy-γ-oxo-α[(3,4,4-trimethyl-2,5-dioxo-1-imidazolidinypmethyl]-1-piperidinebutanamide);
(241) rofecoxib;
(242) RP54745 (4-chloro-5-(3,4-dihydro-1-methyl-2 (1H)-isoquinolinyl)-3H-1,2-dithiol-3-one);
(243) RP66364 (2,4,5-(3-phenylpropyl)-2-thienylbutyoxyacetic acid; a $LTB_4$ antagonist);
(244) RU43526 (a 4-hydroxy-3-quinolinecarboxamide);

(245) RU46057 (2-[1-bis(1-oxopropoxyethyl]-4-hydroxy-N-2-thiazolyl-8-(trifluoromethyl)-3-quinoline carboxamide);
(246) RU54808;
(247) RWJ63556 (N-[5-(4-fluorophenoxy)thien-2-yl] methane sulfonamide; a dual COX-2 selective/5-lipoxygenase inhibitor);
(248) S19812 (N-hydroxy-N-methyl-4-(2,3-bis-(4-methoxyphenyl)-thiophen-5-yl) butanamide, a dual inhibitor of cyclooxygenase and lipoxygenase);
(249) S33516;
(250) salicin;
(251) salicylamide;
(252) salicylsalicylic acid;
(253) satigrel;
(254) SC236 (((E)-(5)-(3,5-di-tert-butyl-4-hydroxybenzylidene)-2-ethyl-1,2-isothiazolidine-1,1-dioxide, also known as S2474);
(255) SC57666 (a selective COX-2 inhibitor);
(256) SC58125 (5-(4-fluorophenyl)-1-[4-(methylsulfonyl)phenyl]-3-(trifluoromethyl)-1H-pyrazole, a selective COX-2 inhibitor);
(257) SC58451 (a selective COX-2 inhibitor);
(258) SD8381 (COX-2 inhibitor);
(259) seprilose (3-O-heptyl-1,2-O-(1-methylethylidene)-α-D-glucofuranose);
(260) SFPP;
(261) SKF105809 (((2-4-methylsulfonylphenyl)-3-(4-pyridyl)-6,7-dihydro-[5H]-pyrrolo[1,2-a]imidazole);
(262) SKF86002 (6-(4-fluorophenyl)-2,3-dihydro-5-(4-pyridinyl)imidazo[2,1-b]thiazole dihydrochloride, an inhibitor of p38 MAP kinase);
(263) sodium salicylate;
(264) sudoxicam;
(265) sulfasalazine;
(266) sulindac;
(267) suprofen;
(268) SVT2016 (5(R)-thiosulfonamide-3-(2H)-benzofuranone);
(269) T3788 (1-(4-aminophenyl)-1-ethanone);
(270) TA60 (2-[4-(3-methyl-2-butenyl)phenyl]propionic acid);
(271) talmetacin;
(272) talniflumate;
(273) tazofelone;
(274) tebufelone;
(275) tenidap;
(276) tenoxicam;
(277) tepoxalin;
(278) tiaprofenic acid;
(279) tiaramide;
(280) tilmacoxib;
(281) tilnoprofen arbamel;
(282) tinoridine;
(283) tiopinac;
(284) tioxaprofen;
(285) tolfenamic acid;
(286) tolmetin;
(287) triflusal;
(288) tropesin;
(289) TY10222 (3-(((2-chloro(1,1-biphenyl)-4-yl)methoxy)methyl-pyridine ethanedioate);
(290) TY10246;
(291) TY10474;
(292) UR8962 (4-[4-(methylsulfonyl)phenyl]-3-[6-(1-pyrrolidinyl)pyridin-3-yl]furan-2(5H)-one);
(293) U91502 ([3-(1,6-dihydro-1-methyl-6-oxo-4-phenyl-2-pyrimidinyl)propylidene]bisphosphonic acid tetraethyl ester);
(294) ursolic acid;
(295) valdecoxib;
(296) WAY120739 (1,8-diethyl-1,3,4,9-tetrahydro-6-(2-quinolinylmethoxy)pyrano [3,4-b]indole-1-acetic acid; a dual inhibitor of 5-lipoxygenase and cyclooxygenase);
(297) WY28342;
(298) WY41770 ((5H-dibenzo[a,d]cyclohepten-5-ylidene)acetic acid);
(299) WY46135 (N-[[(5-chloro-2-benzothiazolypthio] phenylacetyl]-L-cysteine);
(300) ximoprofen;
(301) YS134;
(302) zaltoprofen;
(303) ZD2138 (6-[[3-fluoro-5-(tetrahydro-4-methoxy-2H-pyran-4-yl)phenoxy]methyl]-1-methyl-2(1H)quinolinone);
(304) zidometacin;
(305) zomepirac;
(306) AA961;
(307) acetaminosalol;
(308) AD1590 (2-(8-methyl-10,11-dihydro-11-oxodibenz [b,f]oxepin-2-yl) propionic acid);
(309) AFP802;
(310) aloxiprin;
(311) amfenac sodium;
(312) aminopropylon;
(313) aminopyrine;
(314) amoxiprin;
(315) anirolac;
(316) anitrazafen;
(317) antrafenine;
(318) 2-arylpropionic acids;
(319) azulene sodium sulfonate;
(320) baicalein;
(321) bendazac lysinate;
(322) benorylate;
(323) biphenyl aspirin (2'-acetoxy-biphenyl-2-carboxylic acid);
(324) BPPC;
(325) bromfenac sodium;
(326) broperamole;
(327) bufexamac;
(328) bufezolac;
(329) BW540C;
(330) caffeic acid;
(331) calcium acetylsalicylate;
(332) Chinoin 127;
(333) choline salicylate;
(334) cicloprofen;
(335) cinchophen;
(336) cintazone;
(337) cipamfylline;
(338) clobuzarit;
(339) clometacin;
(340) clonixeril (2,3-dihydroxypropyl 2-(3-chloro-o-toluidino)nicotinate);
(341) cloximate;
(342) CN100 (2-(10,11-dihydro-10-oxo-dibenzo[b,f]thiepin-2-yl)propionic acid);
(343) 4-(4-cyclohexyl-2-methyloxazol-5-yl)-2-fluorobenzenesulfonamide;
(344) cyclooxygenase-1 inhibitors;
(345) delmetacin (UR2310 or 1-benzoyl-2-methylindole-3-acetic acid);

(346) dexindoprofen;
(347) diaryl-5-oxygenated-2-(5H)-furanone;
(348) 2,4-dichlorobenoxaprofen;
(349) difenpiramide;
(350) diflumidone sodium;
(351) 2-(3,5-difluorophenyl)-3-[4-(methylsulfonyl)phenyl]-2-cyclopenten-1-one);
(352) diftalone;
(353) dimethylisopropylazulene;
(354) 5,5-dimethyl-3-isopropyloxy-4-(4'-methylsulfonylphenyl)-2(5H)-furanone;
(355) dimethyl sulfoxide;
(356) DKA9 (4'-chloro-5-methoxy-3-biphenylylacetic acid);
(357) DUP697 (selective COX-2 inhibitor);
(358) EB382;
(359) eicosatriynoic acid;
(360) emorfazone;
(361) enolicam;
(362) ethyleneglycol salicylate;
(363) F1044 (5-[5-(4-chlorophenyl-2-furanyl)]dihydro-2(3H)-furanone);
(364) fenamates;
(365) fenamole;
(366) fenbuprofen;
(367) fenclorac;
(368) fenflumizole;
(369) fenoprofen calcium;
(370) floctafenine;
(371) flunixin meglumine;
(372) flurbiprofen axetil;
(373) fosfosal;
(374) furcloprofen;
(375) glafenine;
(376) glucametacin;
(377) GP53633 (2-t-butyl-4(5)-phenyl-5(4)-(3-pyridyl)-imidazole);
(378) 5(S)-HETE;
(379) 5-HETE lactone;
(380) ibuprofen aluminum;
(381) ibuprofen piconol;
(382) ibuproxam;
(383) imidazole salicylate;
(384) indometacin farnesil;
(385) indomethacin sodium trihydrate;
(386) indoxole (2,3-bis-(p-methoxyphenol)-indole);
(387) intrazole;
(388) ITC1 (2-methoxyethyl isothiocyanate);
(389) ITF182 (imidazole 2-hydroxybenzoate);
(390) JTE522 (4-(4-cyclohexyl-2 methyloxazol-5-yl)-2-fluorobenzensulphonamide);
(391) KB1043 (2-(5-ethylpyridin-2-yl)benzimidazole);
(392) KC8973 (4-butyl-2'-fluorobenzophenone);
(393) ketophenylbutazone (kebuzone);
(394) ketorolac tromethamine;
(395) KME4;
(396) LA2851 (2-4-diamino-7-methyl-pyrazolo (1,5-a) 1,3,5-triazine);
(397) 5-lipoxygenase inhibitors;
(398) lofemizole;
(399) lonazolac calcium;
(400) lotifazole;
(401) lysine acetylsalicylate;
(402) lysine clonixinate;
(403) LU20884 (β-methyl[1,1'-biphenyl]-4-propanenitrile);
(404) M7074 (6-chloro-4-oxyimino-1-phenyl-1,2,3,4-tetrahydroquinoline);
(405) magnesium salicylate;
(406) mefenamic acid aluminum;
(407) mesalamine;
(408) metamizole sodium;
(409) metazamide;
(410) metiazinic acid;
(411) 6-methoxy-2 naphthylacetic acid;
(412) MG18311 (4-((3-hydroxy-1H-indazol-1-yl)phenyl) acetic acid);
(413) mixed PDE3/PDE4 inhibitors;
(414) morniflumate (2-morpholin-4-ylethyl 2-{[3-(trifluoromethyl)phenyl]amino}nicotinate);
(415) morpholine salicylate;
(416) MR714 (2-(4-(2',4'-difluorophenyl)-phenoxy)propionic acid);
(417) MR897 (3-methyl-3-(4-acetylaminophenoxy)-2,4-dioxabenzocyclohexanone-1);
(418) N-acetyl-5-aminosalicylic acid;
(419) 1-naphthyl salicylate;
(420) N-[2-(cyclohexyloxy)-4-nitrophenyl]methanesulfonamide;
(421) neocinchophen;
(422) nictindole;
(423) nifenazone (N-(1,5-dimethyl-3-oxo-2-phenyl-2,3-dihydro-1H-pyrazol-4-yl)nicotinamide);
(424) 2-(2-nitroxy)-butyl 2-acetoxybenzoate;
(425) 2-(2-nitroxymethyl)phenyl 2-acetoxybenzoate;
(426) NO164 (phenyl phosphonate derivative which is a partially selective antagonist of prostaglandin $E_2$);
(427) NPPB (5-nitro-2(3-phenyl) propylamino-benzoic acid);
(428) N-(2-pyridyl)-2-methyl-4-cinnamoyloxy-2H-1,2-benzothiazine-3-carboxamido 1,1-dioxide;
(429) o-(acetoxyphenyl)hept-2-ynyl sulfide (APHS);
(430) olsalazine oxaceprol;
(431) olsalazine sodium;
(432) oxametacin;
(433) oxapadol;
(434) oxicams;
(435) oxyphenthatrazone;
(436) paranylene;
(437) peroxisal;
(438) peroxisal citrate;
(439) phenazone;
(440) phenidone;
(441) phenyl O-acetylsalicylate;
(442) pifoxime;
(443) piketoprofen;
(444) pimeprofen;
(445) piprofen;
(446) piroxicam cinnamate;
(447) proglumetacin maleate;
(448) propyphenazone;
(449) proquazone;
(450) protizinic acid;
(451) QZ16 (2-homopiperidino methyl-3-(o-tolyl)-4-(3H)-6-iodoquinazolone);
(452) R830;
(453) R-enantiomers of acrylacetic acids;
(454) R-enantiomers of aryipropionic acids;
(455) R-enantiomers of thiazinecarboxamides;
(456) RS2131;
(457) RS57067 (COX-2 inhibitor);
(458) RU16029 (4-(2-methyl-3-(4-chlorobenzoyl)phenyl) butanoic acid);

(459) salicylamide O-acetic acid;
(460) SC560 (5-(4-chlorophenyl)-1-(4-methoxyphenyl)-3-(trifluoromethyl)-1H-pyrazole; a cyclooxygenase inhibitor);
(461) SCR152;
(462) sermetacin (N-[[1-(4-chlorobenzoyl)-5-methoxy-2-methyl-1H-indol-3-yl]acetyl]-L-serine);
(463) sodium acetylsalicylate;
(464) sodium thiosalicylate;
(465) sulindac sulfide ((Z)-5-fluoro-2-methyl-1-[p-(methylthio)benzylidene]indene-3-acetic acid);
(466) suxibutazone;
(467) T614 (3-formylamino-7-methylsulfonylamino-6-phenoxy-4H-1-benzopyran-4-one);
(468) TAI901 (4-benzoyl-1-indancarboxylic acid);
(469) tesicam;
(470) tetrydamine;
(471) thromboxane inhibitors;
(472) tiflamizole;
(473) timegadine;
(474) tinoridine hydrochloride;
(475) tomoxiprol;
(476) triethanolamine salicylate;
(477) triflumidate;
(478) trimethazone;
(479) TVX960 (3'-hydroxy-2-[N-methyl-N-(1,1-dimethyl-2-phenethyl)amino] acetophenone);
(480) TVX2706 (3-ethyl-1-(3-nitrophenyl)-2,4(1H,3H)-quinazolinedione);
(481) TZI615 (6,11-dihydro-5-methyl-11-oxo-5H-dibenz[b,e]azepine-2-acetic acid);
(482) U60257 (piriprost potassium salt);
(483) ufenamate;
(484) vedaprofen (4-cyclohexyl-alpha-methylnaphthalene-1-acetic acid);
(485) WY23205 (3[4,5-di-p-chlorophenyloxazol-2-yl] propionic acid);
(486) xenbucin; and
(487) zileuton;
and the salts, solvates, analogues, congeners, bioisosteres, hydrolysis products, metabolites, precursors, and prodrugs thereof.

Other NSAIDs that function as nitric oxide donors are disclosed in U.S. Pat. No. 6,297,260 to Bandarage et al., incorporated herein in its entirety by this reference.

The third agent is a serotonin metabolite. Particularly preferred serotonin metabolites include, but are not limited to, 5-hydroxytryptophan, 5-methoxytryptamine, melatonin, or 5-HIAA (5-hydroxyindoleacetic acid). Preferably, the serotonin metabolite is present in the form of a creatinine sulfate complex, so that particularly preferred serotonin metabolites, in the form of a creatinine sulfate complex, include, but are not limited to, 5-hydroxytryptophan creatinine sulfate complex, 5-methoxytryptamine creatinine sulfate complex, melatonin creatinine sulfate complex, and 5-HIAA (5-hydroxyindoleacetic acid) creatinine sulfate complex. When the serotonin metabolite is added into the composition described above, it can be substantially free of impurities. For example, the serotonin metabolite can have a purity of at least about 80% (e.g., at least about 85%, at least about 90%, at least about 95%, or at least about 99%).

The first, second, or third agents can also be salts, solvates, analogues, congeners, bioisosteres, hydrolysis products, metabolites, precursors, or prodrugs of the compounds described above. Typically, if the first, second, or third agent is not a compound described above, the first, second, or third agent is a salt, prodrug, or solvate of the above-described compounds (i.e., the compounds described above as the first agent, the second agent, or the third agent). A salt can be formed between an anion and a positively charged group (e.g., amino) of an agent. Suitable anions include chloride, bromide, iodide, sulfate, nitrate, phosphate, citrate, methanesulfonate, trifluoroacetate, acetate, chlorophenoxyacetate, malate, tosylate, tartrate, fumarate, glutamate, glucuronate, lactate, glutarate, benzoate, embonate, glycolate, pamoate, aspartate, parachlorophenoxyisobutyrate, formate, succinate, cyclohexanecarboxylate, hexanoate, octonoate, decanoate, hexadecanoate, octodecanoate, benzenesulphonate, trimethoxybenzoate, paratoluenesulphonate, adamantanecarboxylate, glyoxylate, pyrrolidonecarboxylate, naphthalenesulphonate, 1-glucosephosphate, sulphite, dithionate, and maleate. Likewise, a salt can also be formed between a cation and a negatively charged group (e.g., carboxylate) of an agent. Suitable cations include sodium ion, potassium ion, magnesium ion, calcium ion, and an ammonium cation such as tetramethylammonium ion. The agents also include salts containing quaternary nitrogen atoms. Examples of prodrugs include esters and other pharmaceutically acceptable derivatives, which, upon administration to a subject, are capable of being transformed into active compounds. A solvate refers to a complex formed between an active compound and a pharmaceutically acceptable solvent. Examples of pharmaceutically acceptable solvents include water, ethanol, isopropanol, ethyl acetate, acetic acid, and ethanolamine.

The three active agents mentioned above are known drugs or compounds, and are readily available to the public. Some can be purchased from chemical companies, such as Sigma-Aldrich, St. Louis, Mo. Regimens for administering these drug compounds are well known and, if necessary, can be easily re-established.

In one alternative, one or more of the first agent, the second agent, and the third agent can be individually bound to their own individual carrier substances that facilitate the transport of the first agent, the second agent, or the third agent to their intended site of action. For example, only the first agent, only the second agent, or only the third agent can be individually bound to an individual carrier substance. Alternatively, the first agent and the second agent, the first agent and the third agent, or the second agent and the third agent can each be individually bound to an individual carrier substance. As another alternative, the first agent, the second agent, and the third agent can each be individually bound to an individual carrier substance.

The first agent, second agent, or third agent can be either covalently or noncovalently bound to an individual carrier substance. Typically, however, the first agent, second agent, or third agent is covalently bound to an individual carrier substance. Methods for binding the first agent, second agent, or third agent to an individual carrier substance are known in the art. Suitable reagents for cross-linking many combinations of functional groups are known in the art. For example, electrophilic groups can react with many functional groups, including those present in proteins or polypeptides. Various combinations of reactive amino acids and electrophiles are known in the art and can be used. For example, N-terminal cysteines, containing thiol groups, can be reacted with halogens or maleimides. Thiol groups are known to have reactivity with a large number of coupling agents, such as alkyl halides, haloacetyl derivatives, maleimides, aziridines, acryloyl derivatives, arylating agents such as aryl halides, and others. These are described in G. T. Hermanson, "Bioconjugate Techniques" (Academic Press, San Diego, 1996), pp. 146-150, incorporated herein by this reference. The reactivity of the cysteine residues can be optimized by appropriate selection of the neighboring amino acid residues. For example, a histidine residue adjacent to the cysteine residue will increase the reactivity of the cysteine residue. Other combinations of reactive amino acids and electrophilic reagents are known in the art. For example, maleimides can react with amino groups, such as the ε-amino group of the side chain of lysine, particularly at higher pH ranges. Aryl halides can also react with such amino groups. Haloacetyl derivatives can react with the imidazolyl side chain nitrogens of histidine, the thioether group of the side chain of methionine, and the ε-amino group of the side chain of lysine. Many other electrophilic reagents are known that will react with the ε-amino group of the side chain of lysine, including, but not limited to, isothiocyanates, isocyanates, acyl azides, N-hydroxysuccinimide esters, sulfonyl chlorides, epoxides, oxiranes, carbonates, imidoesters, carbodiimides, and anhydrides. These are described in G. T. Hermanson, "Bioconjugate Techniques" (Academic Press, San Diego, 1996), pp. 137-146, incorporated herein by this reference. Additionally, electrophilic reagents are known that will react with carboxylate side chains such as those of aspartate and glutamate, such as diazoalkanes and diazoacetyl compounds, carbonyldilmidazole, and carbodiimides. These are described in G. T. Hermanson, "Bioconjugate Techniques" (Academic Press, San Diego, 1996), pp. 152-154, incorporated herein by this reference. Furthermore, electrophilic reagents are known that will react with hydroxyl groups such as those in the side chains of serine and threonine, including reactive haloalkane derivatives. These are described in G. T. Hermanson, "Bioconjugate Techniques," (Academic Press, San Diego, 1996), pp. 154-158, incorporated herein by this reference. In another alternative embodiment, the relative positions of electrophile and nucleophile (i.e., a molecule reactive with an electrophile) are reversed so that the protein has an amino acid residue with an electrophilic group that is reactive with a nucleophile and the targeting molecule includes therein a nucleophilic group. This includes the reaction of aldehydes (the electrophile) with hydroxylamine (the nucleophile), described above, but is more general than that reaction; other groups can be used as electrophile and nucleophile. Suitable groups are well known in organic chemistry and need not be described further in detail. Additional combinations of reactive groups for crosslinking are known in the art. For example, amino groups can be reacted with isothiocyanates, isocyanates, acyl azides, N-hydroxysuccinimide (NHS) esters, sulfonyl chlorides, aldehydes, glyoxals, epoxides, oxiranes, carbonates, alkylating agents, imidoesters, carbodiimides, and anhydrides. Thiol groups can be reacted with haloacetyl or alkyl halide derivatives, maleimides, aziridines, acryloyl derivatives, acylating agents, or other thiol groups by way of oxidation and the formation of mixed disulfides. Carboxy groups can be reacted with diazoalkanes, diazoacetyl compounds, carbonyldiimidazole, carbodiimides. Hydroxyl groups can be reacted with epoxides, oxiranes, carbonyldiimidazole, N,N'-disuccinimidyl carbonate, N-hydroxysuccinimidyl chloroformate, periodate (for oxidation), alkyl halogens, or isocyanates. Aldehyde and ketone groups can react with hydrazines, reagents forming Schiff bases, and other groups in reductive amination reactions or Mannich condensation reactions. Still other reactions suitable for cross-linking reactions are known in the art. Such cross-linking reagents and reactions are described in G. T. Hermanson, "Bioconjugate Techniques" (Academic Press, San Diego, 1996), incorporated herein by this reference.

The individual carrier substances can be, but are not limited to, antibodies, hormones, receptor agonists or antagonists, or receptors. As used herein, unless further defined or limited, the term "antibody" encompasses both polyclonal and monoclonal antibodies, as well as genetically engineered antibodies such as chimeric or humanized antibodies of the appropriate binding specificity. As used herein, unless further defined, the term "antibody" also encompasses antibody fragments such as sFv, Fv, Fab, Fab' and F(ab)'$_2$ fragments. In many cases, it is preferred to use monoclonal antibodies. Receptors are well known in the art and include G-protein coupled receptors (GPCRs). G-protein coupled receptors (GPCRs) are important signal transducing receptors. The superfamily of G protein coupled receptors includes a large number of receptors. These receptors are integral membrane proteins characterized by amino acid sequences that contain seven hydrophobic domains, predicted to represent the transmembrane spanning regions of the proteins. They are found in a wide range of organisms and are involved in the transmission of signals to the interior of cells as a result of their interaction with heterotrimeric G proteins. They respond to a diverse range of agents including lipid analogues, amino acid derivatives, small molecules such as epinephrine and dopamine, and various sensory stimuli. The properties of many known GPCR are summarized in S. Watson & S. Arkinstall, "The G-Protein Linked Receptor Facts Book" (Academic Press, London, 1994), incorporated herein by this reference. GPCR receptors include, but are not limited to, acetylcholine receptors, β-adrenergic receptors, β$_3$-adrenergic receptors, serotonin (5-hydroxytryptamine) receptors, dopamine receptors, adenosine receptors, angiotensin Type II receptors, bradykinin receptors, calcitonin receptors, calcitonin gene-related receptors, cannabinoid receptors, cholecystokinin receptors, chemokine receptors, cytokine receptors, gastrin receptors, endothelin receptors, γ-aminobutyric acid (GABA) receptors, galanin receptors, glucagon receptors, glutamate receptors, luteinizing hormone receptors, choriogonadotrophin receptors, follicle-stimulating hormone receptors, thyroid-stimulating hormone receptors, gonadotrophin-releasing hormone receptors, leukotriene receptors, Neuropeptide Y receptors, opioid receptors, parathyroid hormone receptors, platelet activating factor receptors, prostanoid (prostaglandin) receptors, somatostatin receptors, thyrotropin-releasing hormone receptors, vasopressin and oxytocin receptors. Agonists and antagonists specifically binding these receptors can be used as individual carrier substances; suitable receptors, agonists, or antagonists can be selected based on their specificity and the location of the receptors in particular cells or tissues.

In addition to the three required agents, the composition used in the methods described in this disclosure can include one or more additional active ingredients.

Typically, the composition comprises 5-5,000 mg of the first agent, 1-5,000 mg of the second agent, and 0.1-1,000 mg of the third agent; or in quantities of the same ratio. Preferably, the composition comprises 5-1,500 mg of the first agent, 1-1,000 mg of the second agent, and 0.1-100 mg of the third agent; or in quantities of the same ratio. More preferably, the composition comprises 5-1,000 mg of the first agent, 1-500 mg of the second agent, and 0.1-50 mg of the third agent; or in quantities of the same ratio.

In one preferred alternative, a composition according to the present invention comprises metformin hydrochloride, aspirin, and 5-hydroxyindoleacetic acid. In another preferred alternative, a composition according to the present invention comprises metformin hydrochloride, aspirin, and 5-hydroxyindoleacetic acid creatinine sulfate complex. The quantities of the first agent, the second agent, and the third agent in these preferred alternatives are as described above.

In one alternative, the composition contains the first, second, and third agents as the only active ingredients. However, in another alternative, the composition can comprise one or more additional active agents as known in the art for the treatment of a disease or condition treatable by the composition as described below.

The composition can comprise a pharmaceutically acceptable carrier, as detailed below. This pharmaceutically acceptable carrier is not to be confused with the individual carrier substances individually bound to one or more of the first agent, the second agent, or the third agent as described above.

In one alternative of a composition according to the present invention, the first agent can be an AMPK activator. Typically, the AMPK activator is selected from the group consisting of metformin, phenformin, buformin, AICAR, thienopyridones, resveratrol, nootkatone, thiazole, adiponectin, thiazolidinediones, rosiglitazone, pioglitazone and dithiolethiones, and the salts, solvates, analogues, congeners, bioisosteres, hydrolysis products, metabolites, precursors, and prodrugs thereof. In another alternative, the first agent can be an ionophore.

The composition can be formulated to treat a disease selected from the group consisting of AIDS, Parkinson's disease, polycystic ovarian syndrome, a hyperproliferative disease, Alzheimer's disease, osteoporosis, sleep apnea, erectile dysfunction, McArdle disease, and a metabolism disorder. If the composition is formulated to treat a hyperproliferative disease, the hyperproliferative disease can be a benign tumor or a malignant tumor. The hyperproliferative disease can be a solid tumor, which can be either benign or malignant. Alternatively, the composition can be formulated to reduce aging or fatigue.

The composition described herein can be used for treating various diseases or disorders, such as metabolic syndrome, obesity, hypertension, diabetes, AIDS, Parkinson's disease, polycystic ovarian syndrome, a hyperproliferative disease (e.g., benign or malignant tumors), Alzheimer's disease, osteoporosis, sleep apnea, erectile dysfunction, McArdle disease, or a metabolism disorder, or for reducing aging or fatigue.

The term "hyperproliferative disease" refers to a disease caused by excess cell proliferation that is not governed by the usual limitation of normal growth. A hyperproliferative disease can include benign tumors and malignant tumors. A hyperproliferative disease can include solid tumors. A "solid tumor", as used herein, refers to an abnormal mass of tissue that usually does not contain cysts or liquid areas. Solid tumors can be benign (not cancerous) or malignant (cancerous).

To practice the method of the present disclosure, an effective amount of the above-described composition can be administered to a subject in need parenterally, orally, buccally, nasally, topically, or rectally. "An effective amount" as used herein refers to the amount of each active agent required to confer a therapeutic effect on the subject, either alone or in combination with one or more other active agents.

Effective doses will vary, as recognized by those skilled in the art, depending on the type or degree of the disorder to be treated; the subject's size, weight, age, and sex; the route of administration; the excipient usage; pharmacokinetic considerations such as kidney or liver function; and the possible co-usage with another therapeutic treatment. The daily dose of the compositions described above can be 5-5,000 mg (e.g., 10-2,500 or 10-3,000 mg) of the first agent, 1-5,000 mg (e.g., 2-1,000 or 2-3,000 mg) of the second agent, and 0.1-1,000 mg (e.g., 1-50 mg) of the third agent.

A subject in need can be identified by a health care professional based on results from a suitable diagnostic method.

The term "treating" or "treatment" used herein refers to administering an above-described compositions to a subject, who has a disease mentioned above, a symptom of such a disease, or a predisposition towards such a disease, with the purpose of conferring a therapeutic effect, e.g., to cure, relieve, alter, affect, ameliorate, or prevent the disease, the symptom of it, or the predisposition towards it. Use of the term "treat," "treating," or similar terminology does not necessarily imply a cure for the disease. The term "reducing fatigue" used herein refers to lessening, ameliorating, or relieving one or more symptoms of fatigue (e.g., low energy, poor endurance, and attention deficits) in a subject. "Reducing aging" refers to lessening, ameliorating, or relieving the deleterious effects of aging (e.g., low vigor, memory loss, weakened vision or hearing, and joint pain) in a subject.

The composition described herein can include a pharmaceutically acceptable carrier to form a pharmaceutical composition. The carrier must be "acceptable" in the sense that it is compatible with the active ingredients of the composition (and preferably, capable of stabilizing the active ingredients) and not deleterious to the subject to be treated. Conventional methods, known to those of ordinary skill in the art of medicine, can be used to administer the pharmaceutical compositions described herein to a subject.

A sterile injectable composition can be a solution or suspension in a non-toxic parenterally acceptable diluent or solvent. The term "parenterally" as used herein refers to subcutaneous, intracutaneous, intravenous, intramuscular, intraarticular, intraarterial, intrasynovial, intrasternal, intrathecal, intralesional, or intracranial injection, as well as any suitable infusion technique. Among the acceptable vehicles and solvents that can be used are mannitol, water, 1,3-butanediol, Ringer's solution, and isotonic sodium chloride solution. In addition, fixed oils are conventionally employed as a solvent or suspending medium (e.g., synthetic mono- or diglycerides). Fatty acids, such as oleic acid and its glyceride derivatives, are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers, which are commonly used in the manufacture of pharmaceutically acceptable solid, liquid, or other dosage forms can also be used for the purpose of formulation.

A composition for oral administration can be any orally acceptable dosage form including capsules, powders, tablets, emulsions and aqueous suspensions, dispersions, and solutions. In the case of tablets or capsules, commonly used carriers or diluents include lactose and corn starch. Lubricating agents, such as magnesium stearate, can be added. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition for topical administration can be prepared in the form of an ointment, a gel, a plaster, an emulsion, a lotion, a foam, a cream of a mixed phase or amphiphilic emulsion system (oil/water-water/oil mixed phase), a liposome, a transfersome, a paste, or a powder.

Any of the compositions described above can also be administered in the form of suppositories for rectal administration. It can also be designed so that the composition is released in the intestine. For example, the composition is confined in a solid subunit or a capsule compartment that has a matrix or a wall or a closure comprising an enteric polymer which dissolves or disperses at the pH of the small or large intestine to release the drug substance in the intestine. Suitable enteric polymers have been described above and also in U.S. Pat. No. 5,705,189, incorporated herein by this reference.

A composition can be included in a drink or food product. Examples include tea (e.g., a tea drink and the contents of a tea bag), soft drinks, juice (e.g., a fruit extract and a juice drink), milk, coffee, cookies, cereals, candies, and snack bars.

The compositions described above can be preliminarily screened for their efficacy in treating an above-described disease or disorder by an in vitro assay and then confirmed by animal experiments and clinical trials. Other methods will also be apparent to those of ordinary skill in the art.

Without further elaboration, it is believed that one skilled in the art can, based on the description herein, utilize the present disclosure to its fullest extent. All of the publications cited herein (including patents and patent applications) are incorporated by reference in their entirety.

Advantages of the Invention

The present invention provides effective compositions and methods for treating a number of diseases and conditions, including AIDS, Parkinson's disease, polycystic ovarian syndrome, a hyperproliferative disease, Alzheimer's disease, osteoporosis, sleep apnea, erectile dysfunction, McArdle disease, and a metabolism disorder, as well as for reducing aging or fatigue. Compositions according to the present invention are well tolerated, substantially free of side effects, and can be administered together with other active ingredients intended to treat these diseases and conditions.

Compositions according to the present invention possess industrial applicability as compositions having pharmacological activity. Methods according to the present invention possess industrial applicability as methods suitable for the preparation of a medicament to treat the diseases and conditions described above.

The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein.

In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of skill in the art upon reviewing the above description. The scope of the invention should therefore, be determined not with reference to the above description, but should instead be determined with reference to the appended claims, along with the full scope of equivalents to which such claims are entitled. The disclosures of all articles and references, including patent publications, are incorporated herein by reference.

What is claimed is:

1. A pharmaceutical composition, comprising:
   (a) a first agent that is an adenosine 5'-monophosphate-activated protein kinase (AMPK) activator selected from the group consisting of metformin, phenformin, buformin, and a salt thereof;
   (b) a second agent that possesses anti-inflammatory activity selected from the group consisting of aspirin, celecoxib, and a salt thereof; and
   (c) a third agent that is a serotonin metabolite selected from the group consisting of 5-hydroxytryptophan, 5-methoxytryptamine, melatonin, 5-hydroxyindoleacetic acid, and a salt thereof.

2. The composition of claim 1 wherein the first agent is selected from the group consisting of metformin, phenformin, buformin, and a salt thereof.

3. The composition of claim 1 wherein the first agent is metformin or a salt thereof.

4. The composition of claim 1, wherein the third agent is selected from the group consisting of 5-hydroxytryptophan, 5-methoxytryptamine, melatonin, and a salt thereof.

5. The composition of claim 1, wherein the third agent is 5-hydroxyindoleacetic acid or melatonin or a salt thereof.

6. The composition of claim 1, wherein the composition comprises metformin or a salt thereof, aspirin or celecoxib, and 5-hydroxyindoleacetic acid or melatonin or a salt thereof.

7. The composition of claim 1, wherein one or more of the first agent, the second agent, and the third agent is individually bound to their own individual carrier substances that facilitate the transport of the first agent, the second agent, or the third agent to their intended site of action.

8. The composition of claim 1, wherein the composition further comprises a pharmaceutically acceptable carrier.

9. The composition of claim 1, wherein the composition contains the first, second, and third agents as the only active ingredients.

10. The composition of claim 1, wherein the composition is formulated to treat a disease selected from the group consisting of a side effect of AIDS treatment, Parkinson's disease, polycystic ovarian syndrome, a hyperproliferative disease, Alzheimer's disease, osteoporosis, sleep apnea, erectile dysfunction, McArdle disease (GSD-V), and a metabolism disorder, or to reduce aging or fatigue.

11. The composition of claim 1, wherein the composition is formulated to treat a side effect of AIDS treatment, a hyperproliferative disease, sleep apnea, McArdle disease (GSD-V), and a metabolism disorder, or to reduce aging or fatigue.

12. The composition of claim 1, wherein the composition is formulated to treat McArdle disease.

13. The composition of claim 1 wherein the composition is formulated to treat a hyperproliferative disease.

14. The composition of claim 1, wherein the composition is formulated to treat a metabolism disorder.

* * * * *